(12) United States Patent
Lee et al.

(10) Patent No.: US 10,436,777 B2
(45) Date of Patent: Oct. 8, 2019

(54) SYSTEM AND METHOD FOR THE DETECTION OF ANALYTES BY CONTROLLED AGGREGATION NANOPARTICLES

(71) Applicant: University College Dublin, National University of Ireland, Dublin, Dublin (IE)

(72) Inventors: Gil Lee, Dublin (IE); Mark Platt, Loughborough Leicestershire (GB)

(73) Assignee: University College Dublin, National University of Ireland, Dublin, Dublin (IE)

( * ) Notice: Subject to any disclaimer, the term of this patent is extended or adjusted under 35 U.S.C. 154(b) by 0 days.

(21) Appl. No.: 14/363,756

(22) PCT Filed: Dec. 5, 2012

(86) PCT No.: PCT/EP2012/074483
§ 371 (c)(1),
(2) Date: Jun. 6, 2014

(87) PCT Pub. No.: WO2013/083621
PCT Pub. Date: Jun. 13, 2013

(65) Prior Publication Data
US 2014/0315328 A1    Oct. 23, 2014

(30) Foreign Application Priority Data

Dec. 6, 2011 (GB) .................................. 1120965.7

(51) Int. Cl.
*G01N 33/543* (2006.01)
*B03C 1/32* (2006.01)
(Continued)

(52) U.S. Cl.
CPC ....... *G01N 33/54306* (2013.01); *B03C 1/032* (2013.01); *B03C 1/24* (2013.01);
(Continued)

(58) Field of Classification Search
CPC .. G01N 33/54306; G01N 33/543; B03C 1/24; B02C 1/32
(Continued)

(56) References Cited

U.S. PATENT DOCUMENTS

2002/0146745 A1*  10/2002  Natan ................. G01N 33/538
                                                                        435/7.1
2007/0148044 A1    6/2007  Murata
(Continued)

FOREIGN PATENT DOCUMENTS

JP    2006-104255 A    4/2006
JP    2010-007169 A    1/2010
(Continued)

OTHER PUBLICATIONS

Yu et al., "Multiplex Biosensor Using Gold Nanorods," Jan. 15, 2007, vol. 79, No. 2, pp. 572-579.*
(Continued)

*Primary Examiner* — Tracy Vivlemore
*Assistant Examiner* — Nam P Nguyen
(74) *Attorney, Agent, or Firm* — Holzer Patel Drennan

(57) ABSTRACT

A method for detecting an analyte in a sample, the method comprising contacting the analyte in a sample with nanoparticles comprising a capture probe for capturing said analyte, the capture probe being configured to act as a center for controlled aggregation of nanoparticles with said analyte to form an aggregate of predefined form, detecting the analyte by detecting the shape and/or size of the aggregate is provided. Also provided are nanoparticles comprising a capture probe for capturing an analyte, wherein the capture (Continued)

probe is configured to act as a center for controlled aggregation of nanoparticles with the analyte to form an aggregate of particular detectable size and/or shape, and an assay.

12 Claims, 12 Drawing Sheets

(51) Int. Cl.
  *B03C 1/24* (2006.01)
  *B03C 1/032* (2006.01)
  *B03C 1/28* (2006.01)
  *G01N 27/74* (2006.01)

(52) U.S. Cl.
  CPC .......... *B03C 1/288* (2013.01); *G01N 27/745* (2013.01); *G01N 33/54326* (2013.01); *G01N 33/54346* (2013.01); *B03C 2201/18* (2013.01); *B03C 2201/24* (2013.01); *B03C 2201/26* (2013.01)

(58) Field of Classification Search
  USPC .......................................... 436/501; 435/6.12
  See application file for complete search history.

(56) References Cited

U.S. PATENT DOCUMENTS

| 2007/0202495 | A1* | 8/2007 | Mayer | G01N 33/48721 |
|---|---|---|---|---|
|  |  |  |  | 435/5 |
| 2014/0227679 | A1* | 8/2014 | Lee et al. | 435/6.12 |

FOREIGN PATENT DOCUMENTS

| WO | 2006-074130 A2 | 7/2006 |
|---|---|---|
| WO | 2008-048221 A2 | 4/2008 |
| WO | 2010-092333 A1 | 8/2010 |
| WO | WO-2011050070 A1 * | 4/2011 |
| WO | 2013-004852 A2 | 1/2013 |

OTHER PUBLICATIONS

Oh et al. "Separation of Tricomponent Protein Mixtures with Triblock Nanorods", JACS, vol. 128, pp. 11825-11829, published Aug. 22, 2006.*
Lee et al., "Multicomponent Magnetic Nanorods for Biomolecular Separations", Angew. Chem. Int. Ed., vol. 43, pp. 3048-3050, published 2004.*
Dictionary.com, "Rod", retrieved from the internet <http://www.dictionary.com/browse/rod>, print retrieved on Aug. 4, 2017.*
Oxforddictionaries.com, "Predefined", retrieved from the internet <https://en.oxforddictionaries.com/definition/predefined>, print retrieved on Aug. 4, 2017.*
Vogel et al., "Quantitative Sizing of Nano/Microparticles with a Tunable Elastomeric Pore Sensor", Anal. Chem., vol. 83, pp. 3499-3506, published Mar. 24, 2011.*
Wang et al. (Nanotechnology, vol. 17, pp. 3375-3379, published 2006) (Year: 2006).*
Platt, et al., "Resistive Pulse Sensing of Analyte-Induced Multicomponent Rod Aggregation Using Tunable Pores," Small-Journal, vol. 8, No. 15, Aug. 6, 2012, pp. 2436-2444.
Saleh, et al., "Antibody-coated gold nanoparticles immunoassay for direct detection of Aeromonas salmonicidia in fish tissues," Journal of Fish Diseases, vol. 34, No. 11, Nov. 1, 2011, pp. 845-852.
International Search Report and Written Opinion of PCT/EP2012/074483 dated Mar. 27, 2013, 13 pages.

* cited by examiner

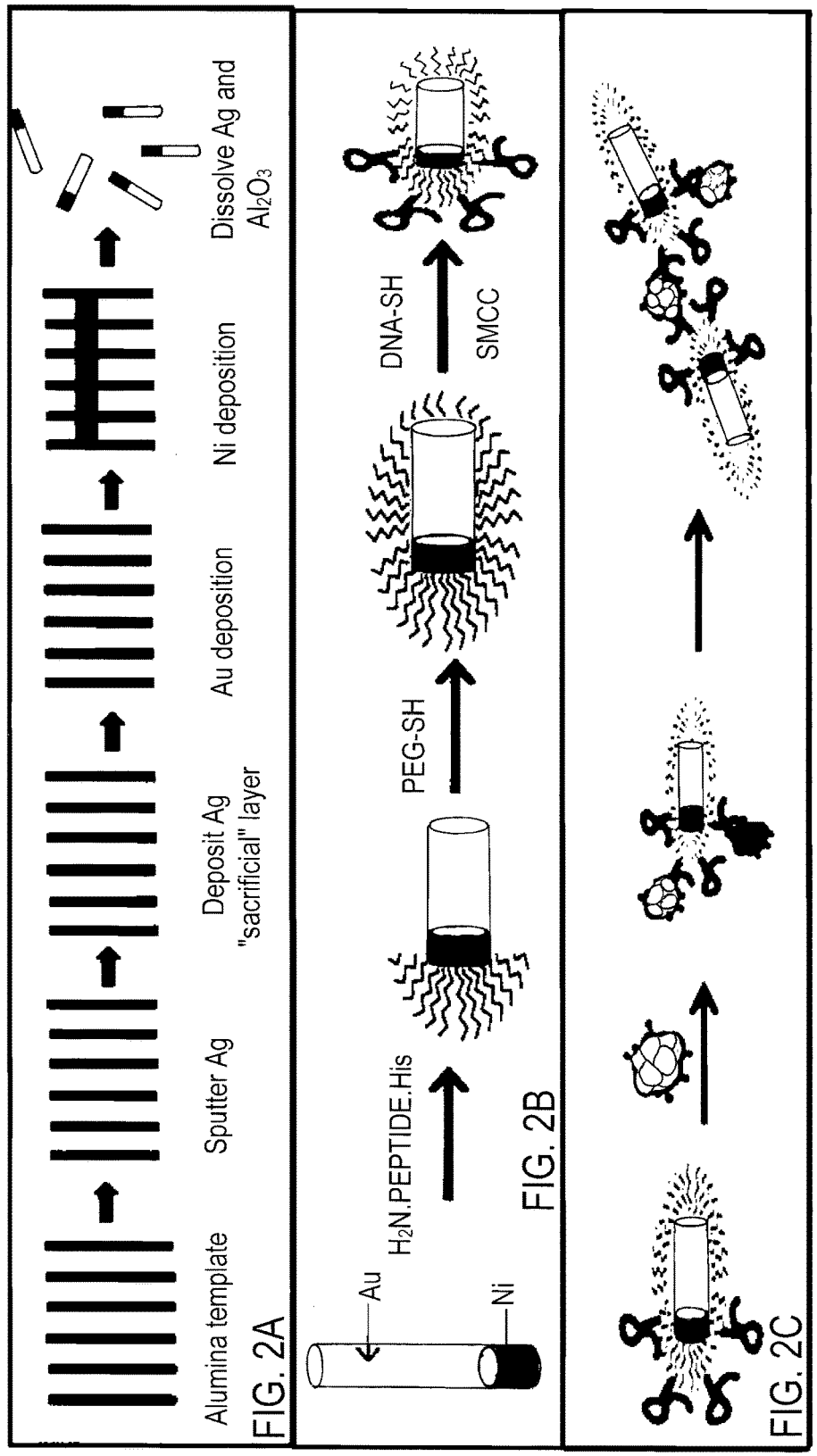

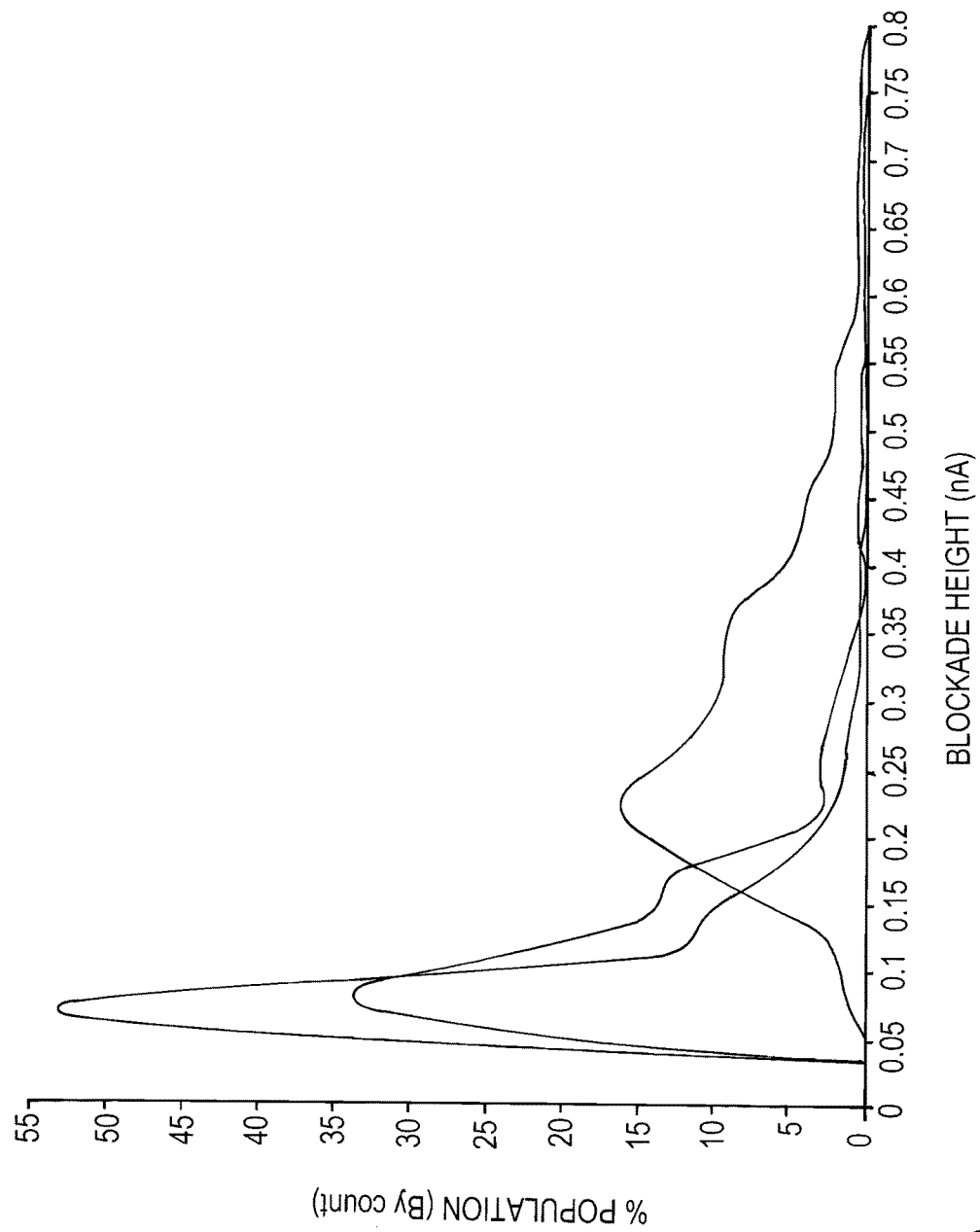
FIG. 5A(1)

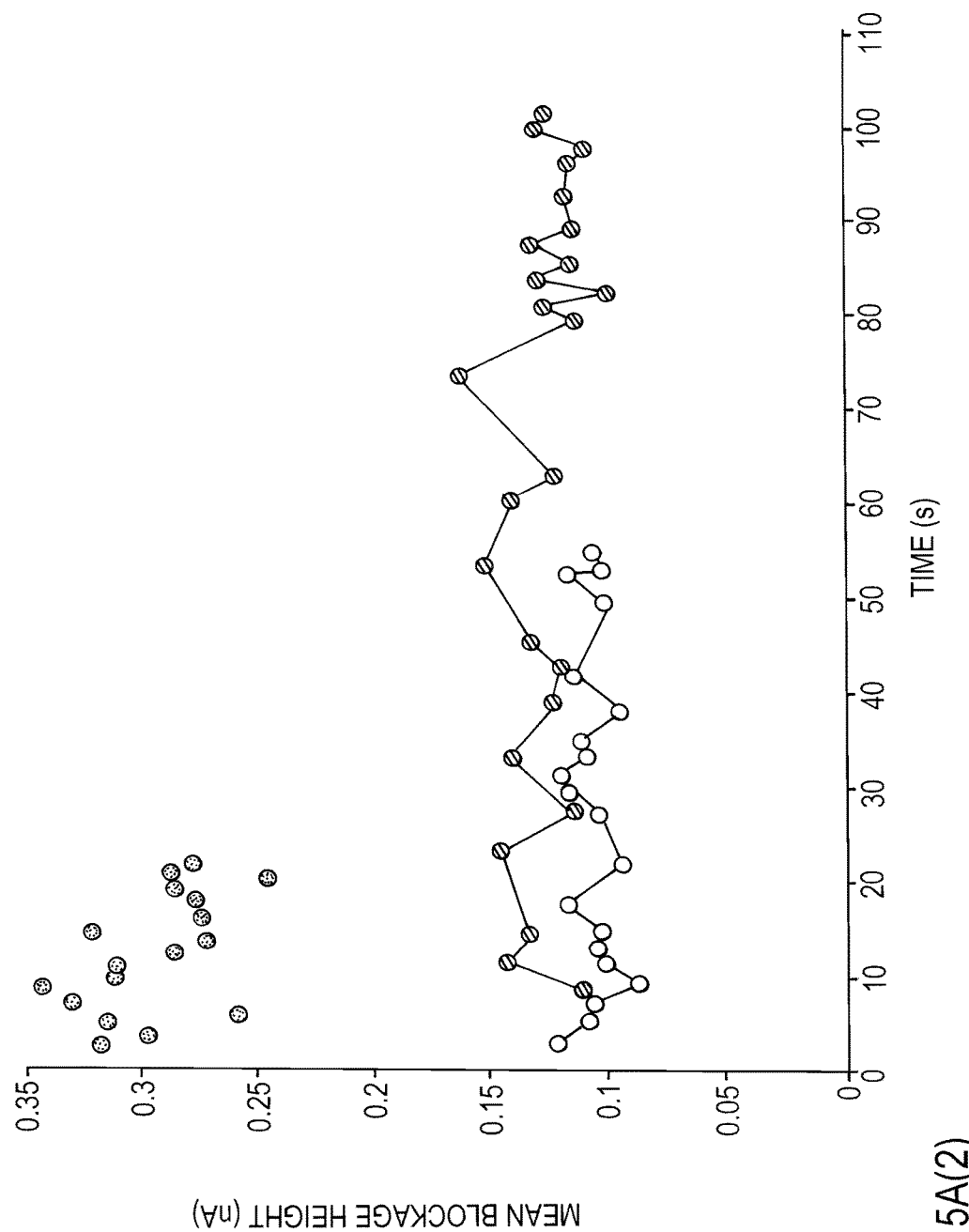
FIG. 5A(2)

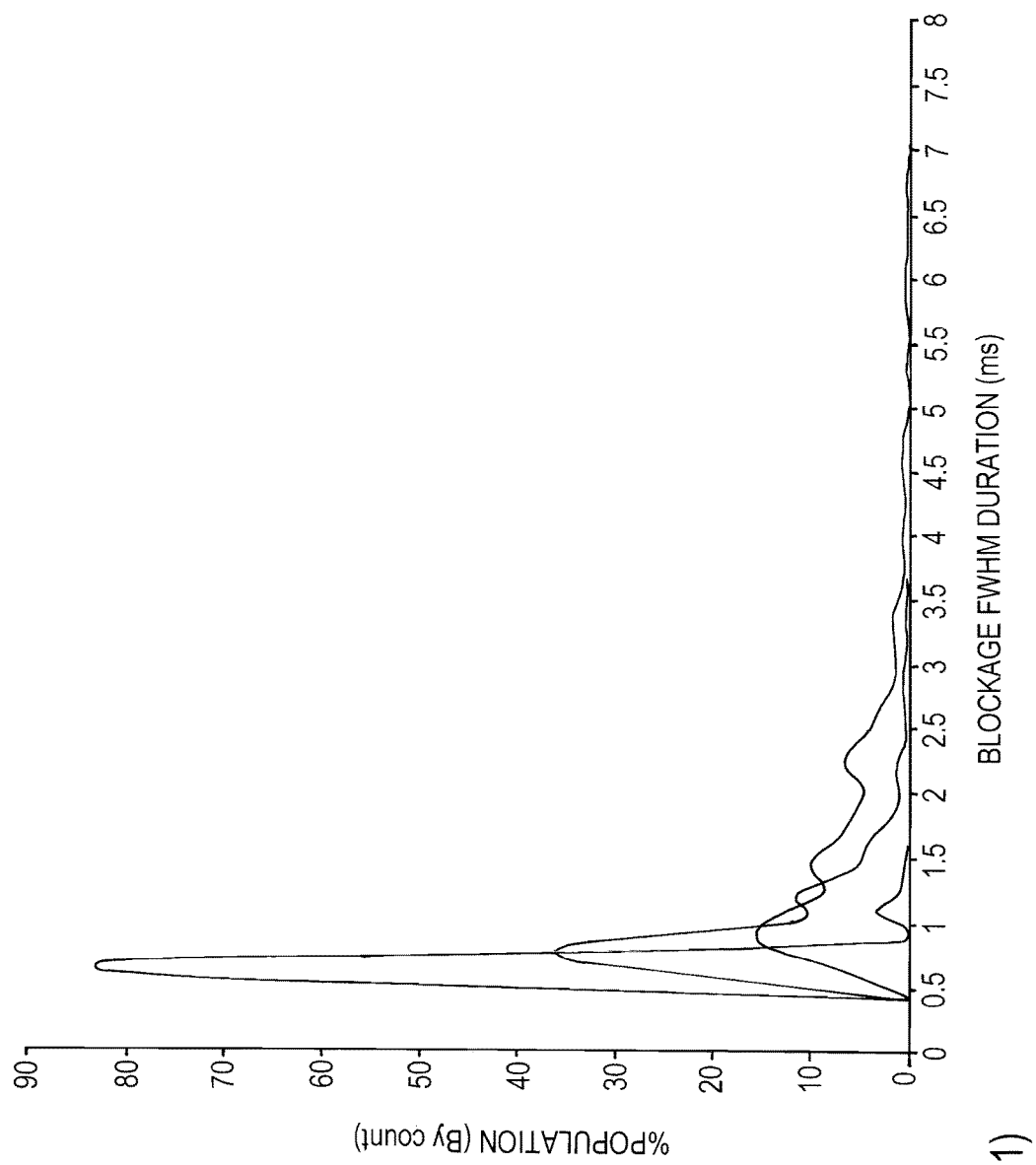
FIG. 5B(1)

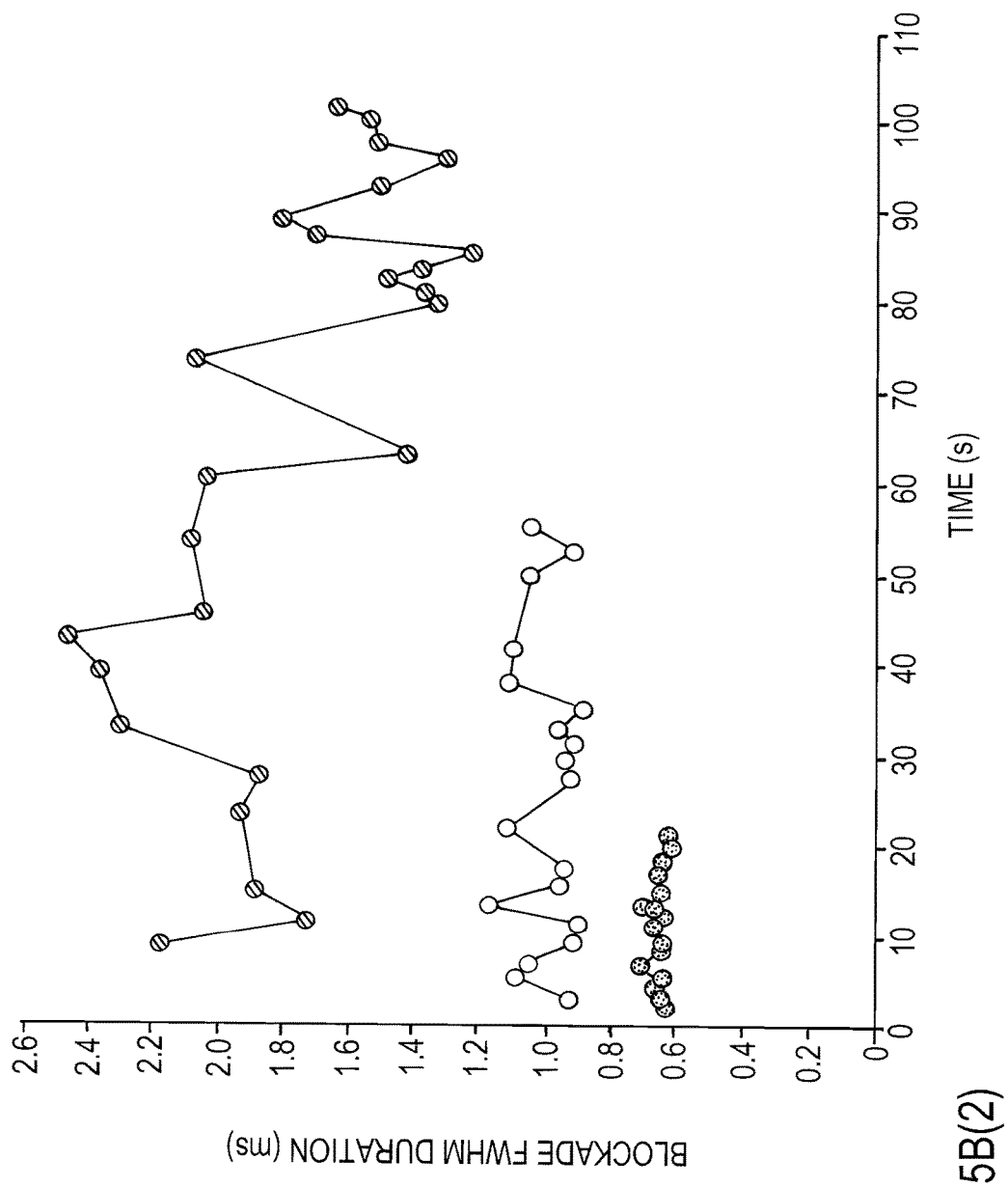
FIG. 5B(2)

SYSTEM AND METHOD FOR THE DETECTION OF ANALYTES BY CONTROLLED AGGREGATION NANOPARTICLES

PRIORITY CLAIM

The present application is a U.S. 371 National Phase Patent Application and claims benefit of Patent Cooperation Treaty application No. PCT/EP2012/074483, entitled "SYSTEM AND METHOD FOR THE DETECTION OF ANALYTES BY CONTROLLED AGGREGATION NANOPARTICLES" and filed on 5 Dec. 2012, which takes priority from U.K. Patent Application 1120965.7 filed on 6 Dec. 2011, all of which are incorporated herein by reference in their entirety.

BACKGROUND

Aggregation assays are often prepared using spherical beads, whereupon the addition of the analyte causes the beads to aggregate. This change in particle size and behaviour is typically monitored using light scattering, absorption, or fluorescence to enable detection of an analyte. Multiplex detection may be achieved by either changing the diameter of the particles or one of their physical properties such as the colour it absorbs or emits light. However, there is a need for an improved method of detection of analytes in particular multiplex detection.

SUMMARY

According to the present specification there is provided a method for detecting an analyte in a sample, the method comprising contacting the analyte in a sample with nanoparticles comprising a capture probe for capturing said analyte, the capture probe being configured to act as a centre for controlled aggregation of nanoparticles with said analyte to form an aggregate of predefined form, detecting the analyte by detecting the shape and/or size of the aggregate.

In one embodiment, the nanoparticles comprise rod shaped particles. In another embodiment the nanoparticles comprise an aspect ratio greater than 1. In one embodiment, the nanoparticles may comprise a curved form or surface. In another embodiment the nanoparticles may comprise a generally cylindrical form. In another embodiment nanoparticles may comprise a generally spherical form. In one embodiment, detecting the analyte comprises detecting the change in shape and/or size of the particles in the sample resulting from the aggregation with the analyte. The aggregate may have a predefined shape. The aggregate may have a predefined size. In one arrangement the nanoparticles may be configured to aggregate end to end with an analyte to form an aggregate of detectably increased length. In another arrangement the nanoparticles may be configured to aggregate side by side with an analyte to form an aggregate of detectably increased size or width. The location of the capture probe on the nanoparticle may be varied as required to control aggregation and the form of the resulting aggregate. Detecting an analyte may comprise detecting the size of aggregates passing through a detector. Detecting an analyte may comprise detecting the shape of aggregates passing through a detector.

Detecting an analyte may comprise detecting the full width half maximum (FWHM) signal, the signal being indicative of the time taken for the particle or aggregate to traverse the detector. The full width half maximum (FWHM) signal providing an indication of particle or aggregate length. Detecting an analyte may comprise detecting the change in base line current $\Delta ip$ signal, the signal being indicative of the blockade event or blockade height. The percentage (%) change in the base line current $\Delta ip$ signal providing an indication of particle volume. Detecting the analyte may further comprise counting the aggregates present in the sample.

According to another aspect there is provide a nanoparticle comprising a capture probe for capturing an analyte, wherein the capture probe is configured to act as a centre for controlled aggregation of nanoparticles with the analyte to form an aggregate of particular detectable size and/or shape.

The nanoparticle may comprise a rod shaped particle. The nanoparticles may comprise an aspect ratio of greater than 1. The diameter and length of the nanoparticle may be varied as required during manufacture. The nanoparticle may comprise a multi-component rod. The nanoparticle may further comprise a segment defining a location for the capture probe. The nanoparticle may comprise an Ni segment. The location and size of the segment may be controlled as required during manufacture to provide for controlled aggregation of the nanoparticles with an analyte. The location and size of the capture probe may be controlled as required during manufacture to provide for controlled aggregation of the nanoparticles with an analyte. In one arrangement the location and size of the Ni segment may controlled as required during manufacture to provide for controlled aggregation of the nanoparticles with an analyte. The nanoparticle may comprise a curved form or surface. The nanoparticle may comprise a generally cylindrical form. The nanoparticles may comprise a generally spherical form.

In a first arrangement the capture probe may be provided at one end of the rod shaped particle. The nanoparticles being configured to aggregate end to end with an analyte and similar nanoparticle. In a second arrangement the capture probe may be provided between the rod ends and spaced apart from the rod ends. The nanoparticle being configured to aggregate side by side with an analyte and similar nanoparticle.

The multi-component rod may further comprise a component selected to provide optical and/or magnetic characteristics. The surface of the nanoparticle may comprise a surface modification. The modification may be configured to allow capture of DNA or to allow capture of proteins.

The nanoparticles/s may manufactured by template deposition. The dimensions of the nanoparticles/s may be controlled by template deposition methods for example by control of both the reaction time and the template used. The template may comprise a membrane having regular cylindrical pores, the diameter of the pores controlling the diameter of the growing particle/s. The length of the particles may be determined by the total charge passed during the course of the electro-deposition. The material within the nanoparticles/s may be controlled by varying the solution and potential under which the reaction takes place.

According to a further aspect an assay for determining an analyte may be provided, the assay using nanoparticles according to the present specification comprising a capture probe for capturing said analyte characterized in that said nanoparticles comprise rod shaped particles, said nanoparticles being configured to aggregate to form with said analyte a complex of detectable size and/or shape.

According to a further aspect there is provided a method of detecting an analyte in a sample comprising the steps of:

providing nanoparticles having at least one analyte capture probe fixed thereto, the analyte capture probe being capable of binding an analyte;

introducing the nanoparticles into the sample;

allowing the analyte to bind to the at least one analyte capture probe on two nanoparticles to form an analyte bound nanoparticle complex; wherein the nanoparticles are configured to aggregate in a controlled manner with the analyte to form a complex of predetermined shape and/or size;

detecting the analyte bound nanoparticle complex based on the size and/or shape of the complex; and detecting the presence of the analyte.

The nanoparticles may comprise rod shaped nanoparticles.

In one arrangement the presence of the analyte is detected by a nanopore detection system. The size of each complex entering the nanopore detection system as determined by the magnitude of current dip may be measured. The volume a particle or particles obstruct as it traverses the pore being related to the peak height or blockade height is measured. The full width half maximum (FWHM) being an indication of the time taken for the particle to traverse the pore may be measured. Further the particles passing through the nanopore detection system may be counted sequentially. The method may further comprise determining a concentration of the analyte.

The nanoparticles may comprise first and second rod shaped nanoparticles of first and second lengths, the first and second rod shaped nanoparticles having capture probes configured to capture different analytes and further being configured to aggregate to form different complexes, wherein the complexes are of different shape and/or size.

The nanoparticles may comprise rod shaped nanoparticles and spherical nanoparticles, the rod shaped nanoparticles and spherical nanoparticles comprising capture probes configured to capture different analytes and further being configured to aggregate to form different complexes, wherein the complexes are of different shape and/or size.

BRIEF DESCRIPTION OF DRAWINGS

FIG. 2 Schematic of the particle synthesis. FIG. 2A—Example template deposition method for producing rod shaped particles of an embodiment according to the present specification including the steps of (i) providing an alumina template, (ii) sputtering with Ag, (iii) depositing Ag "sacrificial layer, (iv) Au Deposition, (v) Ni deposition and (vi) dissolving Ag and $Al_2O_3$. FIG. 2B—Overview of the surface chemistry stages (i) providing Au rod with Ni segment, Ni segments are modified with a His-tagged peptide, the Au segments are modified with PEG-SH molecules, DNA-SH SMCC. FIG. 2C—Example schematic of the assay, showing end on end aggregation of two nanoparticles (rods) with analyte;

FIG. 3A—image of a suitable example detection system in this case a nanopore detection instrument. In the middle of the septum an individual pore enables particles to pass through the membrane. Side on image on the membrane and pore, the sample is placed into the upper fluid cell, and the particles move down through the pore under the influence of gravity into the lower fluid cell.

FIG. 4A, Mode $\Delta i_p$ values as pore size is varied, fixed potential of 0.12V, FIG. 4B, Mode FWHM values as pore size is varied, fixed potential of 0.12V. FIG. 4C, $\Delta$ip histogram for the samples run at a stretch of 44.5 mm in part A. FIG. 4D FWHM histogram for samples run at a stretch of 44.5 mm part B.

FIG. 5A1 Height (Peak/Blockade height) (nA) versus % population. FIG. 5A2—average size/mean blockade height (y axis) over the course of the experiment in seconds (x axis). FIG. 5B1 FWHM (ms) versus % population; FIG. 5B2 Blockade FWHM vs Time (s)

FIG. 8A, AuNi rods, 1.23 µm in length (CV 20%, Ni content 15% by length), 400 fM, % Change $\Delta i_p$ and FWHM as assay time is increased in the absence of an analyte. FIG. 8B, Same rods as A, assay time 10 mins. Ni segments functionalised with Avidin. Dashed lines represent a 10 min assay with a non biotinylated target. FIG. 8C, AuNiAu rods, 0.82 µm in length (CV 14%, Ni content 18% by length), 500 fM, assay time 10 mins. FIG. 8D, AuNi rods, 1.1 µm in length (CV 20%, Ni content 14% by length), 150 fM assay time 10 mins. Ni segments functionalised with PDGF aptamer. The circled data points plotted at 100 fM indicate the change in FWHM and $\Delta$ip (blockade height or peak height) for the same rods using a control protein

DETAILED DESCRIPTION

The present specification provides a method for the detection of the analytes based on the use of nanoparticles which are configured for controlled aggregation with analytes to form complexes of different shape and/or size. The present specification also provides a multiplex method for the detection of analytes, based on the analyte induced nanoparticle aggregation.

Figure 1:
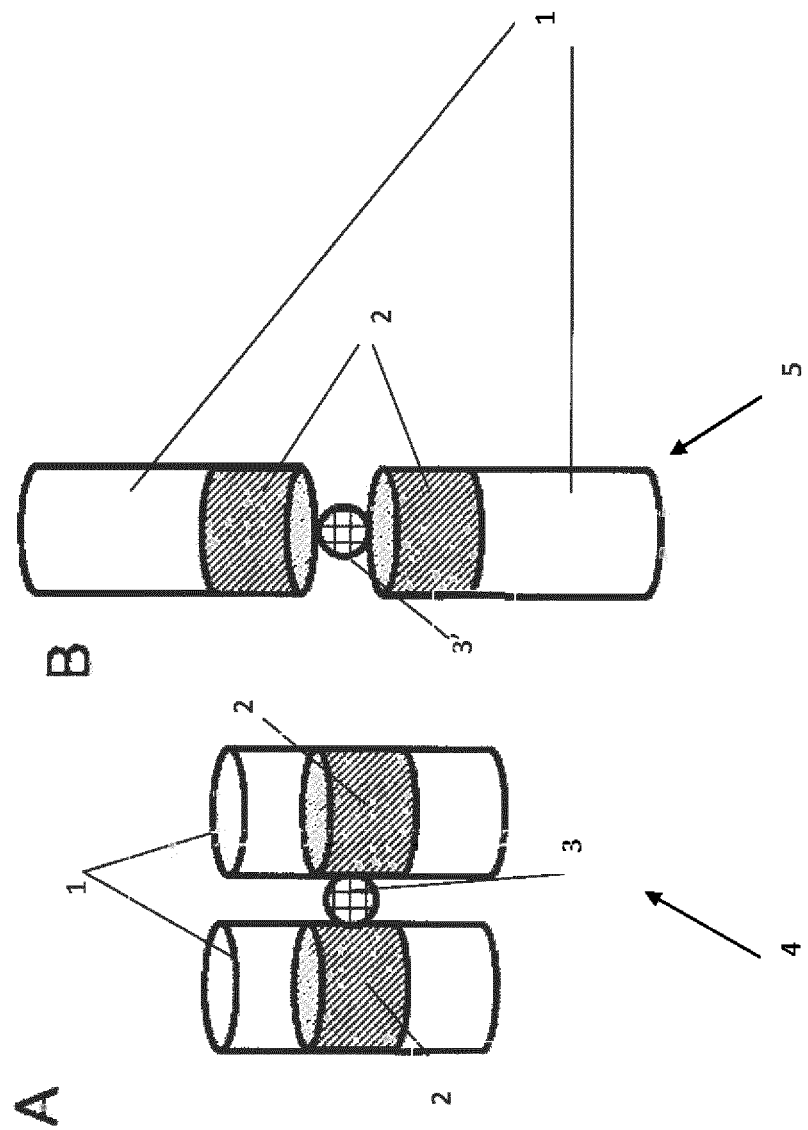
FIG. 1 Schematic of two assay techniques a—aggregation leading to an increase in size, b—End-on-End aggregation.

Referring to the drawings and initially in particular to FIG. 1 exemplary nanoparticles 1 according to the invention are described. Nanoparticles 1 comprise a capture probe 2 for capture of an analyte 3. The particles 1 are configured to aggregate in a controlled manner with analyte 3 to form complexes or aggregates of different size and/or shape the resulting complexes or aggregates being detectable using a suitable detection system. The capture probe 2 acts as the centre for controlled aggregation of the nanoparticles 1 with analyte 3. By controlling the surface chemistry of the particles 1 during manufacture and in particular the location of the capture probe 2 thereon, the particles 1 may be configured to form aggregates of different shape and/or size, as required upon addition of analyte 3. The location of the capture probe on the nanoparticle is controllable and selectable. The capture probe is located at a specified area on the nanoparticle. By control of the location of the capture probe on the nanoparticle, it is possible to provide for controlled aggregation of the nanoparticles with an analyte. It is accordingly possible to monitor the concentration of an analyte 3 in a sample by monitoring the changes in particle or in the particle aggregate size or/and shape in a sample upon addition of nanoparticles 1. A count of the particles and/or aggregates provides information on concentration of an analyte in a sample.

In the exemplary arrangement of FIG. 1, the nanoparticles 1 comprise substantially rod shaped particles or cylindrical form nanoparticles. Rod shaped particles 1 are effectively configured to aggregate at different orientations depending on the location of the capture probe 2 thereon. Referring to exemplary FIG. 1 two alternative orientations of nanoparticles 1 aggregated with an analyte 3 are shown. The nanoparticles may be configured to aggregate end to end with analyte (as illustrated in FIG. 1B) to form a complex or aggregate 5 of greater length, or side by side with an analyte to form a complex or aggregate 4 of greater size or width (as illustrated in FIG. 1A).

The term rod shaped particles has been used herein to generally describe the particles with dimensions having aspect ratio greater than 1, it will be appreciated that particles of different suitable form having aspect ratio greater than 1 may also be used. It will be appreciated that nanoparticles of suitable alternative form may also be used. For example, nanoparticles comprising cylindrical nanoparticles or ellipsoid nanoparticles may also be used. The nanoparticles may have a major axis and a minor axis. The nanoparticles may have a curved surface. The form of the nanoparticles is clearly not limited to those of a particular lateral or longitudinal cross-section. This specification relates to nanoparticles having a form such that when aggregates are formed, as described, the aggregates have a detectable or distinguishable size and/or shape. The nanoparticles are provided with a capture probe at a controlled location thereon for example, a specified segment or localized capture probe. The nanoparticle may comprise a segment or sector defining a location for the capture probe. The terms particles, rod shaped particles, cylindrical shaped particles, and nanoparticles have been used to describe the nanoparticles of the present specification. It will be appreciated that nanoparticles of aspect ratio of 1, or substantially 1, or generally spherical nanoparticles may also be used. Use of spherical beads is described later in the specification when data based on detection of spherical beans is compared with that based on detection of the nanoparticles of rod shaped or cylindrical form. Spherical beads may for example be configured such that a capture probe is provided at a specific limited location or localized at a specific area or sector thereof such as to provide controlled aggregation of nanoparticles with an analyte to form an aggregate of nanoparticles of detectable shape and/or size, as described above, clearly may also be used. Further, suitable alternative forms of nanoparticles particles include particles for which it is possible to control location of the capture probe thereon, or, for which the capture probe is provided in a specific location only rather than generally thereon. The nanoparticles comprise localised or locally defined surface chemistries.

The nanoparticles 1 are multi-component particles. The surface chemistry of the nanoparticles 1 is controlled as required during formation. Further the nanoparticles 1 of rod shaped or cylindrical form have two physical dimensions which can be controlled and varied during manufacture, namely diameter and length. FIG. 2A shows a template deposition method for producing nanoparticles 1 of rod shaped form. FIG. 2B shows an overview of the surface chemistry stages and FIG. 2C shows a schematic of an assay. The dimensions of the exemplary rod shaped nanoparticles 1 may be controlled by template deposition methods for example by control of both the reaction time and the template used. The template may comprise a membrane having regular cylindrical pores. An exemplary template may have pores having an average diameter of 250 nm, and this dimension ultimately controls one dimension—the diameter of the growing particle. The length of rod shaped particles 1 may be determined by the total charge passed during the course of the electro-deposition. The material within the rod can be controlled by varying the solution and potential under which the reaction takes place. The rod shaped nanoparticles 1 of FIG. 1 and FIG. 2 comprise Au and further comprise a segment 6 defining a capture site for capture probe 2. The locations and forms of the segment 6 and the capture probe 2 on the surface of the rod shaped particle 1 can accordingly be controlled and varied during manufacture. The control of the location and form of the capture probe 2 provides the necessary control of the manner in which the rod shaped particles 1 aggregate with an analyte and resulting control of the form of the aggregates. In the exemplary embodiment the segment 6 comprises a Nickel (Ni) segment. The Ni segment 6 is here modified with a His-tagged peptide, and the capture probe 2 for the analyte is then attached to the surface.

Referring to FIG. 1B, an arrangement is shown in which capture probe 2 is located at one end of the rod shaped particles 1, and the particles are configured to aggregate with an analyte oriented end to end resulting in complex 4 of increased length. In an alternative as shown in FIG. 1A the capture probe 2 is located between the ends of the rod 1 and spaced apart from the ends of the rod. In this case the particles 1 will not aggregate end to end but rather are configured to aggregate oriented side by side resulting in a complex 4 of increased size or width. Thus rod shaped particles 1 of the same size and form may be used to form aggregates of different shape and size.

The provision of the Ni segment 6 makes handling the rods much easier, during any surface chemistry modifications and subsequent wash stages the rods can be separated from solution using a simple hand held magnet as opposed to centrifugation. The Ni segment provides a loci for the capture probe for the analyte. This results in a "sticky" Ni segment that captures the analyte and acts as the centre for aggregation. It will be appreciated that while in the exemplary arrangement according to the specification Nickel (Ni) is used other suitable components could be included or used in place of the Ni. The nanoparticle 1 is a multi-component particle and additional components within a rod 1 can be selectively altered using specific chemistries. In the example described, the nanoparticles comprise Au and a Ni segment which is modified with a His-tagged peptide, it is known that the His tagged peptides will only attach to the Ni surface and not the Au, having first modified the Ni with the peptide the capture probe for the analyte can then be attached to the surface. Other peptides are known to attach to metals such as Co, Fe, Au, Ag, Pd, and Pt and could easily be incorporated into the rods 1 instead of or alongside the Ni segment.

The rod shaped nanoparticles 1 may further be modified to incorporate additional required physical properties such as an optical or magnetic characteristic, by controlling the materials the rods are composed of The optical or magnetic properties may be configured for detection.

The arrangement of the present specification and the rod shaped nanoparticles 1 provides for multiplex detection in a number of alternatives. While assays with spherical shaped beads where only the diameter can be varied for multiplexing, the rod shaped nanoparticles 1 have two physical dimensions which can be changed, diameter and length. Thus rod shaped nanoparticles 1 of different aspect ratios can be assigned to capture different and the frequency of their aggregates counted using a suitable detection system. Additionally the rod shaped nanoparticles 1 are multi-component particles and it is possible to control the location of the capture probe in the rods surface and to direct the shape of the aggregation of the particles. The different forms of the aggregates of particles 1 are detectable and distinguishable. Detection of analyte 3 is achieved using a suitable detection system namely a system which can distinguish and count the different types of particle aggregates based on different shape and/or size.

While in the exemplary embodiment as illustrated nanoparticles, in this case rod shaped or cylindrical shaped nanoparticles have been used, it will be appreciated that nanoparticles of suitable alternative form for example, of spherical form may be used. As noted above the diameter of the spherical nanoparticle may be varied as required to provide different nanoparticles for the purposes of multiplex detection. The nanoparticles, similarly to the rod shaped or cylindrical particles described above, may be provided with for example, a Nickel (Ni) segment to provide a loci for the capture probe for the analyte. This results in a "sticky" Ni segment that captures the analyte and acts as the centre for aggregation. It will be appreciated that while in the exemplary arrangement according to the specification Nickel (Ni) may be used other suitable components could be included or used in place of the Ni. The nanoparticle 1 is a multi-component particle and additional components within a nanoparticle may be selectively altered using specific chemistries. In the example described, the nanoparticles comprise Au and a Ni segment which is modified with a His-tagged peptide, it is known that the His tagged peptides will only attach to the Ni surface and not the Au, having first modified the Ni with the peptide the capture probe for the analyte can then be attached to the surface. Other peptides are known to attach to metals such as Co, Fe, Au, Ag, Pd, and Pt and could easily be incorporated into the nanoparticle instead of or alongside the Ni segment. The nanoparticles may further be modified to incorporate additional required physical properties such as an optical or magnetic characteristic, by controlling the materials the nanoparticles are composed of. The optical or magnetic properties may be configured for detection.

Figure 3A:
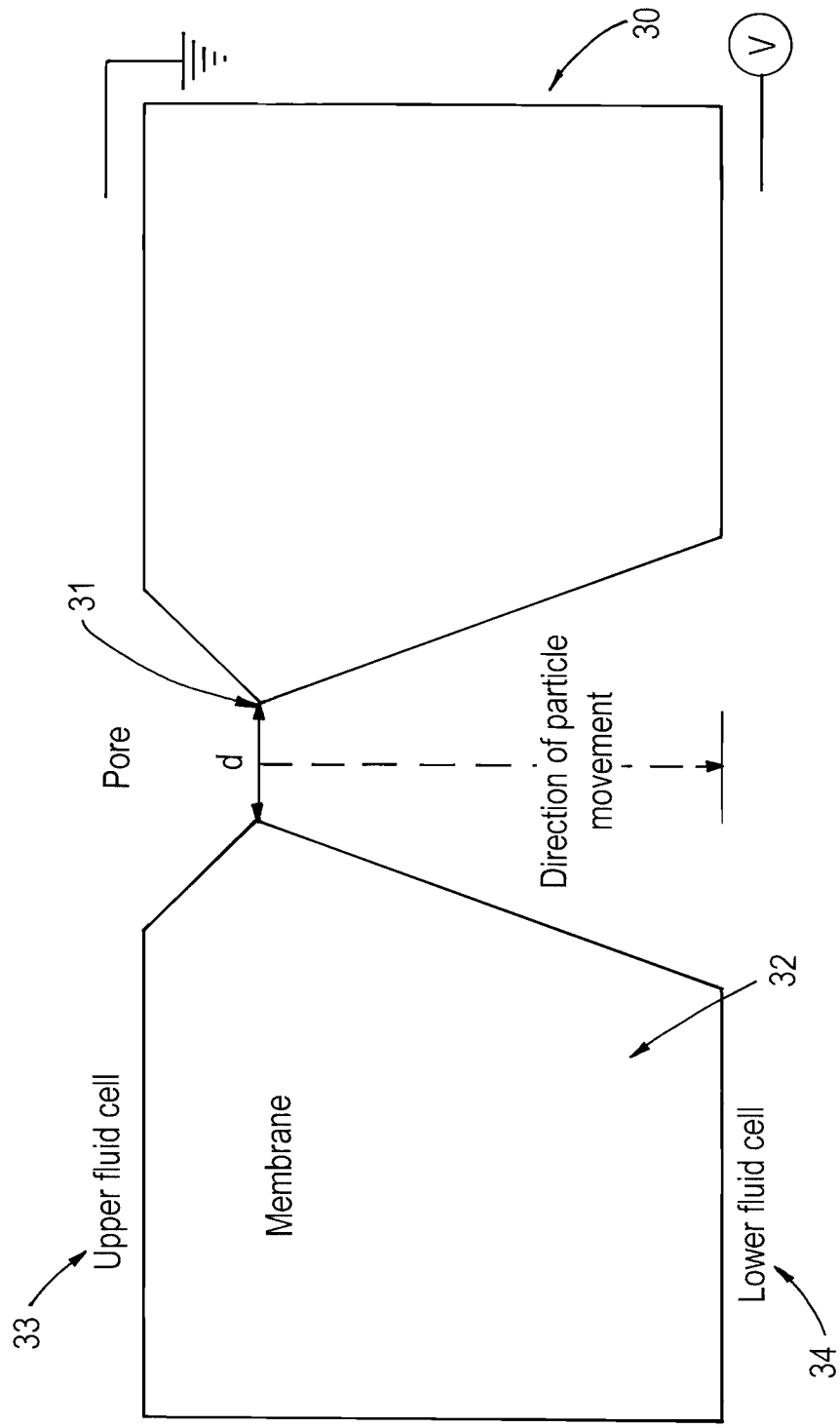
FIGS. 3A and B Overview of the nanopore detection process.
Figure 3B:
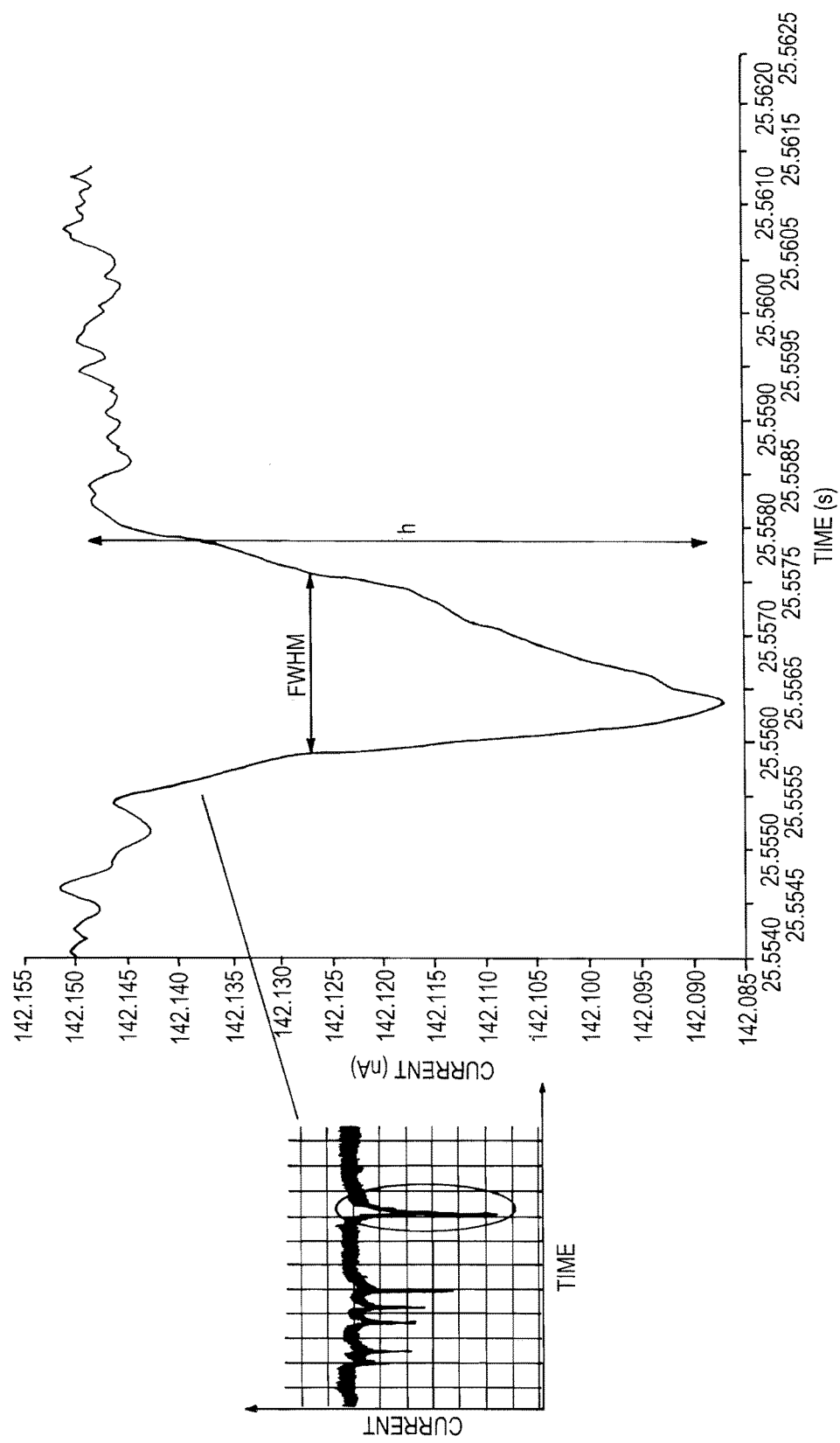
FIG. 3B—shows an example of baseline current and "blockade" events (dips in current) that are caused by particles. Each dip contains information on particle size and FWHM.

Referring to FIG. 3 a detection system 30 comprising a nanopore is shown. In brief the system comprises a pore 31 of known dimensions. Further for example, a tunable nanopore system may be used. The detection system 30 is not described herein in detail. In brief, the system 30 comprises a pore 31 comprising a membrane 32. In the case of a tunable nanopore system the membrane may be stretched in a controlled and reversible manner to change the pore geometry as required. The pore is filled with a conducting media and a potential is applied between electrodes on either side of the opening to establish a current flow through the pore known as the baseline current ip which is proportional to applied voltage and electrolyte conductivity. The nanopore system 30 is used to monitor the behavior of the nanoparticles 1 as they move across the membrane pore opening 31, illustrated in FIG. 3A as having width d. The sample is placed into the upper fluid cell 33, and the particles move down through the pore under the influence of gravity into the lower fluid cell 34. During operation a current change $\Delta ip$ i.e. blockade height or peak height or height is registered when a particle moves through the pore causing a blockade event to occur. The volume the particle obstructs as it traverses the pore is related to peak height. Based on the proportionality between blockade height or peak height ($\Delta ip$) and particle volume, measurement of the % change in blockade or peak height ($\Delta ip$) is used to provide an indication of particle size. The full width half maximum, FWHM indicative of duration time or time taken particle traversing the pore is also measured. The FWHM measurements for rod shaped particles are fundamentally different to those for example for spherical particles. The form of the rod shaped particles leads to an increase in dwell time within the pore attributable to the rod shaped particles moving through the pore in an orientated manner. A measurement of the FWHM is used to provide an indication of particle length.

A method is provided for detecting analytes in a sample. The method comprises providing nanoparticles 1 comprising a capture probe 2 for capturing the analyte 3, wherein the capture probe 2 is configured to act as a centre for controlled aggregation of nanoparticles 1 with the analyte to form aggregated particles of particular shape and/or size upon addition to the sample.

A nanopore system 30 is used to monitor the nanoparticles 1 passing therethrough. Blockade events indicated by % change in $\Delta ip$ (peak height) and the duration or dwell time, FWHM, are monitored and measured. The % change in $\Delta ip$ is used to indicate particle volume and the FWHM is used to indicate particle length. The nanopore system is accordingly used to detect the presence of aggregates of different form. A count of the aggregates passing through the system is also maintained.

While a suitable detection system as described above comprises a nanopore system, it will be appreciated that suitable alternative systems may also be used. For example, a tunable pore in which the dimensions of the pore may be varied may be used. Alternatively a detector device having different fixed pores may be used. It will be appreciated from the foregoing description that a suitable detector is a detector which may be configured to detect the different aggregates and to distinguish the different aggregates/different shapes and/or sizes.

The method may be applied to the multiplex detection of two or more analytes. According to a first approach, a method of detection of two different analytes is based on detection of complexes of different shape and size formed by nanoparticles 1 of the same size and form. In this case nanoparticles 1 of the same size and form are provided, each having a different capture probe 2 configured for the capture of different analytes 3. The capture probes 2 are configured to provide for the controlled aggregation of the nanoparticles by the location of the capture probe on the surface of the particle. The capture probe 2 of the nanoparticle 1 of the first type may be located at the end of the nanoparticle such that the nanoparticles 1 of the first type will aggregate end to end with the analyte resulting in an aggregate of increased length. The capture probe 2 of the nanoparticle 1 of the second type may be located between the ends of the nanoparticle such that the nanoparticles 1 of the second type will aggregate side by side with the analyte resulting in an aggregate of increased width. The nanoparticles of the first and second type are added to the sample. The sample is monitored using the nanopore system. The presence of rod shaped nanoparticles 1 of type 1 are configured aggregate end-on-end with an analyte (Type 1, FIG. 1B), is indicated by a simultaneous increase in blockade or peak height Δip and FWHM. The presence of rod shaped nanoparticles 1 of type 2 which are configured to aggregate in a side-on configuration with analyte (type 2, FIG. 1A), is indicated by a change in peak height $\Delta i_p$ in the monitored signal.

In an alternative, the detection of different analytes may be based on detection of rod shaped particles 1 of first and second type having different aspect ratios each assigned to capture a different analyte. For example, rod shaped particles 1 of different length may be used each having capture probes 2 for different analytes. The rod shaped particles 1 may further be configured to aggregate end to end. Thus detection may be based on detection of complexes of different lengths. In the example 1 described in further detail below rod shaped particles 1 having lengths of the order of 2 microns and 5 microns respectively are used. The presence of aggregates of different length is indicated based on the simultaneous changes in Δip and FWHM signals measured, indicative of increased volume and length. A nanopore detection system or a tunable nanopore detection system may be used.

Figures 4A, 4B, 4C, 4D:
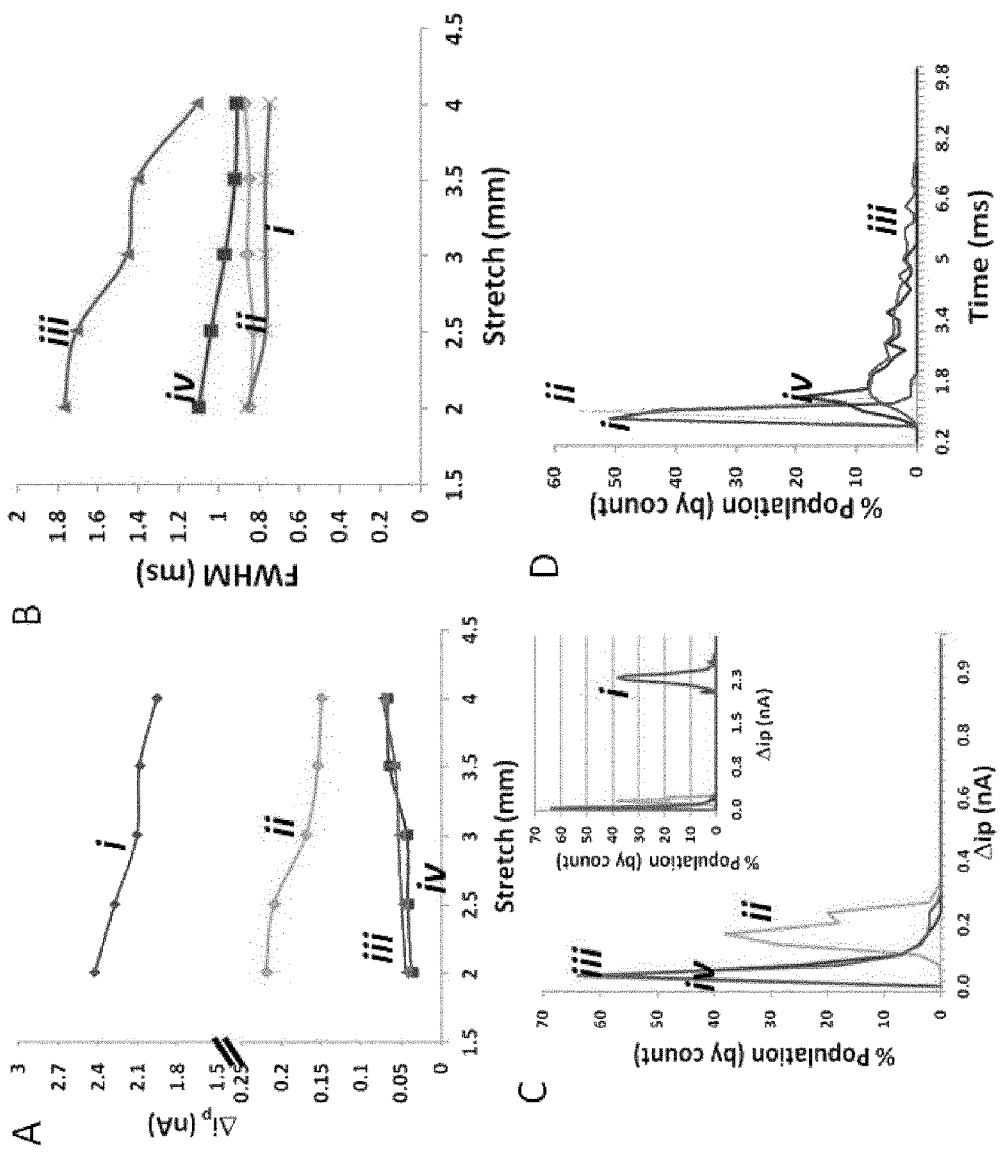
FIGS. 4A, 4B, 4C and 4D. Purple (i)=sphere (2 µm diameter), Green (ii)=sphere (0.955 □µm diameter), blue (iii)=Au rod (4.7 µm length-CV 14%, 290 nm diameter-CV 15%), Red=(iv) Au rod (2.15 µm length-CV 20%, 325 nm diameter-CV 14%).
Figure 6:
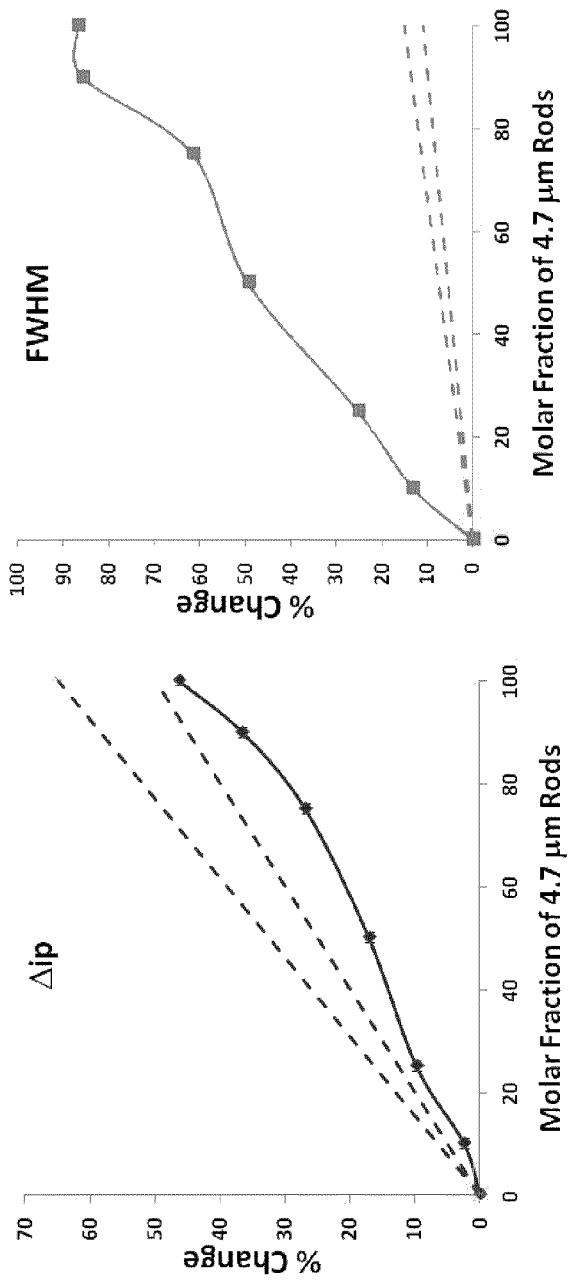
FIG. 6 Changes in (height/blockade height or peak height) $\Delta$ip, and blockade FWHM, as mole fraction of 4.7 µm rods is increased from a solution containing initially only the 2.15 µm rods. Dashed regions indicate the maximum and minimum values predicted from the model given the CV of the particle set. Error bars show the d25 and d75 values for the measured population.

Referring to FIGS. 4, 5 and 6 the use of a nanopore system to detect analytes using rod shaped particles and a method according to the present specification is further described. Firstly the signal from rod shaped particles 1 as they traverse the pore was characterized, the $\Delta i_p$ is proportional to the volume/size of the particle, and that the rod length was monitored via the FWHM. By utilizing the two clear signals from rod shaped particles 1 an agglutination assay was designed, two capture probes 2 were chosen to demonstrate the assay format. The first was the model biotin-avidin system, the second capture probe 2 chosen was a DNA aptamer. The aptamer chosen here was the 35 mer sequence which binds to the protein platelet derived growth factor, PDGF-BB, with a $K_d$~0.1 nM. Template deposition allows for nanoparticles to be produced with dimensions that are controlled by both the reaction time, as well as the template itself. The pores within the $Al_2O_3$ membrane have an average diameter of circa 300 nm, and determined the diameter of the growing particle. The length of the rod was determined by the total charge passed during the course of the electrodeposition. The composition of material within the multi-component rod 1 was controlled by varying the plating solution as well as the potential under which the reaction takes place. In the example arrangement of FIGS. 4 to 6 a tunable pore detection system having the ability to stretch the pore during use, as described above was used to detect aggregates of particles 1 with analytes. The measurements (FIG. 4) record the $\Delta i_p$ and FWHM as the pore size was increased. Two sizes of spheres, 0.95 pm and 2 μm in diameter, and rods composed of Au, 2.1 μm and 4.7 μm in length were used. In FIG. 4A the $\Delta i_p$ can be seen to decrease for the spherical particles as the pore size is increased. In contrast the Δip for the rods increased with stretch. It is clear from FIG. 4B that across all stretches the two rod shaped particles produce a FWHM value much larger than the spherical beads. The 4.7 μm rods record the largest FWHM values which implies the longest translocation time. A simple control assay to determine the sensitivity of the tunable pore system to solutions that contained mixtures of the 2.1 μm and 4.7 μm Au rods was performed.

Referring to FIG. 5A Height (nA) versus % population. Insert—average size (y axis) over the course of the experiment in seconds (x axis). FIG. 5A FWHM (ms) versus % population; i=1 micron sphere; ii=4.7 micron long rod; and iii=2 micron long rod Referring to FIG. 6, initially a solution containing 2.1 μm rods was analyzed, the molar fraction of the 4.7 μm rod was then increased from 0 to 10, 25, 50, 75, 90 and 100% the modal $\Delta i_p$ (FIG. 6A) and FWHM (FIG. 6B), values are plotted as % change from the initial 2.1 μm rod solution. The FWHM values increase with increasing fraction of 4.7 μm rods.

Example Avidin-Biotin Assay.

Figure 7:
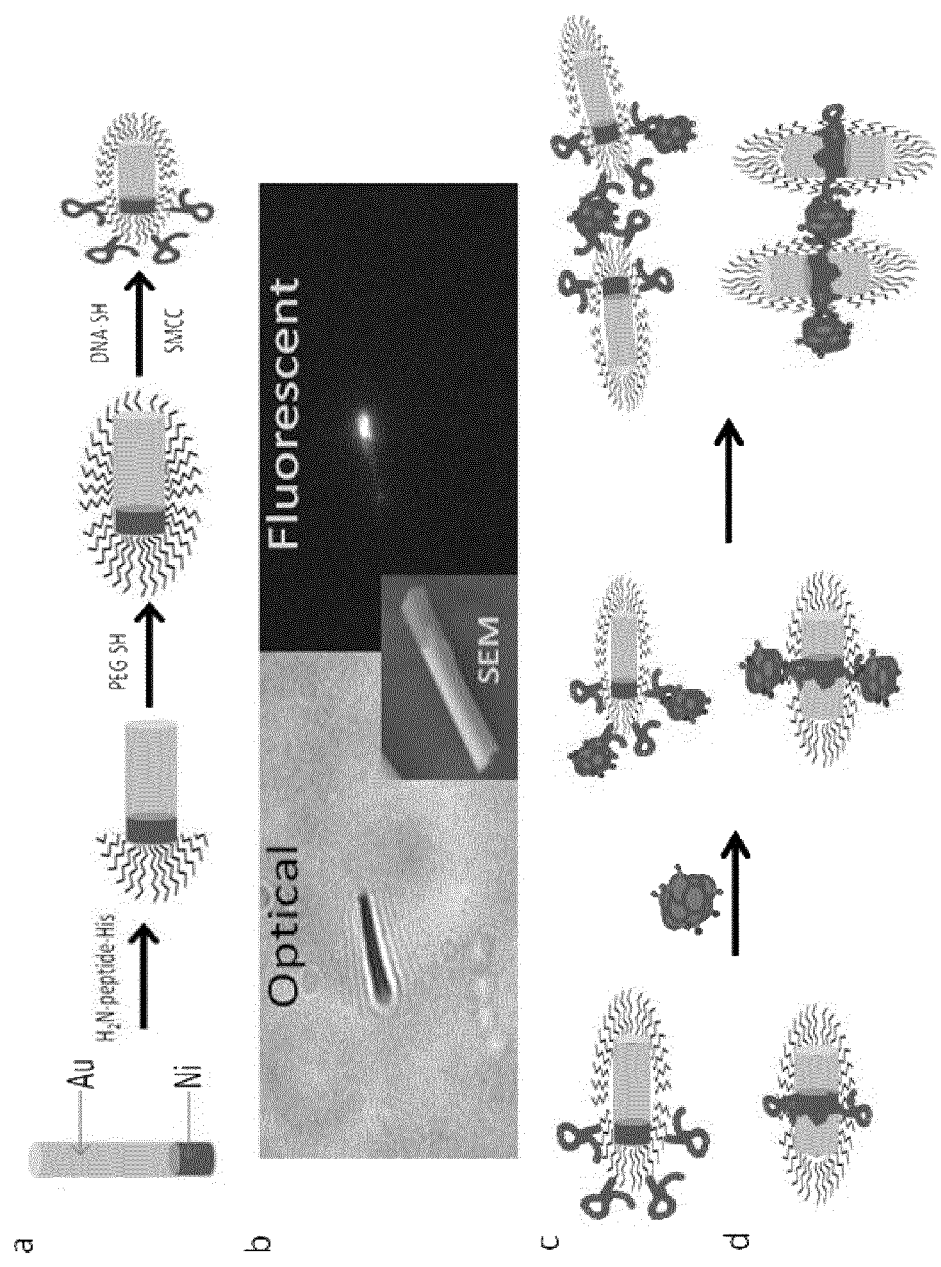
FIG. 7a—Overview of the surface chemistry modifications and assays. 7a—The surfaces of the Ni segments are modified with a His-tagged peptide, the Au segments are modified with PEG-SH molecules. 7b—Confirmation of localised surface chemistries with fluorescent modified Nickel (Ni) segments. 7c—Schematic of the aggregation assay via "end-on-end" aggregation 7d—Schematic of the aggregation assay via "Side-on" aggregation.

A further example assay according to the present specification is described with reference to FIG. 7A schematic of the rod shaped nanoparticles 1 used for the agglutination assays are shown in FIG. 7. By controlling the orientation in which the rods are made to aggregate, rods 1 of similar aspect ratios are used to produce alternate signal responses in the presence of a target analyte 3, thus making agglutinations assays easier to multiplex with the rod shaped particles 1 and a tunable pore system. For rods aggregated end-on-end, (FIG. 7C), a simultaneous increase in blockade/peak height Δip and FWHM is expected, where rods are made to aggregate in a side-on configuration (FIG. 7D) only a change in peak height $\Delta i_p$ is expected. The capture probes were conjugated to the Ni surface using a His-modified peptide. The peptides contained a 6×Histidine tag on one end and 4 residual amine groups on the opposite, for conjugation to the capture probe of interest. Two different capture probes were conjugated to the rods the first was an avidin protein, these particles were used as a control assay to monitor the changes in behavior in the presence of a biotinylated protein target. To first confirm the surface chemistry performed as shown in the schematic, the Ni modified avidin particles were incubated for 5 mins with a solution of biotinylated-FITC. A localized fluorescent signal confirmed its success, FIG. 7B.

The effect of this was to cause the slow aggregation of the particles if they were left in solution without sonication for periods longer than 20 minutes. FIG. 7A shown the % change in $\Delta i_p$ and FWHM for 1 μm rods, end functionalized with Ni, in a buffered solution. The solution was placed on a rotating wheel and sampled at 5 min intervals. A slight increase in $\Delta i_p$ and FWHM was measured. It was clear that the Ni causes the nonspecific aggregation of the particles at short reaction times, however it should occur at a level low enough not to be the dominant signal during the aggregation in the presence of an analyte. A 10 min assay time was chosen based upon the calculated mutual diffusion coefficient of $5.6 \times 10^{-8}$ $cm^2 s^{-1}$ for rods 1 μm in length and 150 nm in radius, given a concentration of particles circa 300-500 fM, these conditions should be sufficient time for the assay to be completed, given that the rate determining step of the diffusion of the analyte to the rod. In each assay a blank was run to allow the % change for FWHM and Δip to be calculated. FIG. 7B shows the change in Δip and FWHM for an assay using end functionalized rods, where the Ni segment was conjugated to avidin. The rods were first sonicated, an aliquot was then drawn from the stock solution, to this was added an equal volume of analyte solution, the final dilutions and concentrations of the particles are plotted in FIG. 7. A similar protocol was used for the rods containing a Ni segment in the middle, results from the side-on assay are shown in FIG. 7C.

PDGF Assay.

Figures 8A, 8B, 8C, 8D:
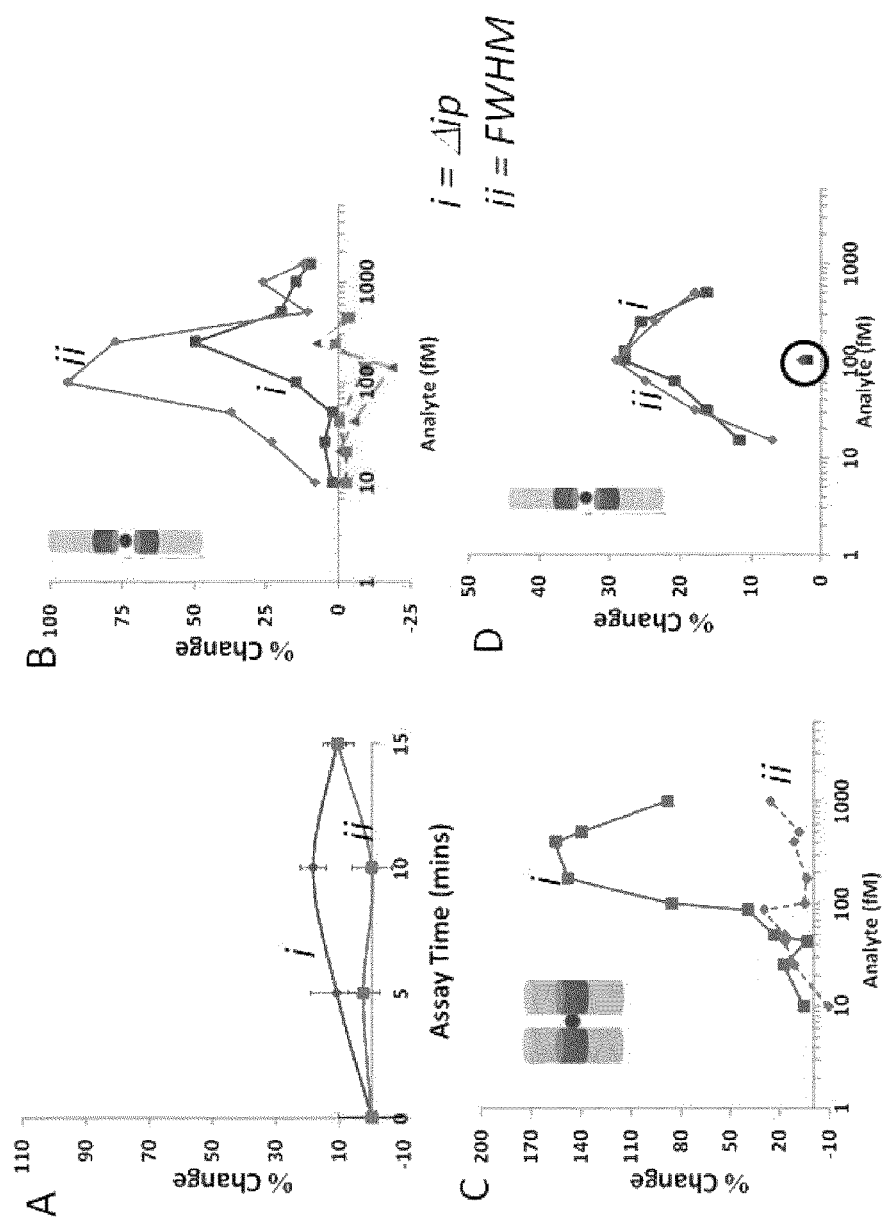
FIGS. 8A, 8B, 8C and 8D. Performed using a NP1000, stretch=44.5 mm=Potential=0.14, red lines indicate $\Delta i_p$, blue lines indicate FWHM.

An end-on-end assay format for the detection of PDGF is described with reference to FIG. 8. It is known that that the aptamer binds to the protein in a 2:1 ratio. As in the case of the avidin example above, an increase in both the $\Delta$ip and FWHM was shown FIG. 8D, a control assay for the same rods using a different protein (BSA) produced small changes in FWHM and $\Delta i_p$, (FIG. 8D circled data points), demonstrating that the aggregation was not nonspecific. Despite the 2.1 μm rod having a similar dimension as the 2 μm diameter sphere, the rod particles produce a FWHM significantly higher (FIG. 4B). As the rod length is increased the FWHM values also increase and is attributed to the fact that the rods pass through the pore vertically.

Example

Agglutination assay. Rods were synthesized containing a Ni segment, to which was first conjugated the avidin protein. Increasing the concentration of biotinylated-BSA in the solution causes two trends in the recorded values to be noted (FIG. 8B). First, both the $\Delta i_p$ and FWHM values rise, the increase in signal continues to a concentration of 250 fM, before the number of binding sites on the particles start to become saturated a hook effect is observed. Second, the change in the FWHM is the dominant signal, as the rods aggregate forming longer rods. The increase in rod length, as demonstrated within the control assay (FIG. 4B) results in changes in FWHM that are much larger then $\Delta$ip. Rods from the same synthesis batch were also exposed to a non-biotinylated protein target, a small percentage change in both $\Delta i_p$, and FWHM was observed, (FIG. 8B (dashed lines)). The results from the side-on assay are shown in FIG. 8C, an increase in analyte concentration causes a clear increase in $\Delta i_p$, where as the FWHM does not change significantly. This side-on aggregation has the effect of forming rods with larger diameters but a constant FWHM. Similar behaviors were recorded for the PDGF assay using the end-on-end format. The sensitivity is as low as 10 fM, using the same capture probe, however the percentage change in both the FWHM and $\Delta$ip is much lower than the example using avidin-biotin.

The present specification accordingly provides an improved system and method for detection of analytes. Rod shaped nanoparticles according to the specification are provided. The nanoparticles are configured to aggregate in a controlled manner in the presence of an analyte. The form of the aggregates is detectable and distinguishable. Analytes are detected using a suitable detection system, for example in this case a tunable nanopore system is used. Unlike detection formats such as light scattering of colorimetric assay where the physical properties of the entire population of particles are measured simultaneously, with the methods described each of the particles/aggregates is measured independently as they traverse the pore, building up readings that represent the population. Accordingly the method is advantageously accurate and sensitive.

The movement of rod shaped particles through a pore detection system has been shown. It has been shown that as the rods traverse the pores the $\Delta i_p$ is sensitive to the volume of the particle and the FWHM values provide an indication of the length, as by increasing the length of the rod/aggregate a much slower translocation time is recorded. An agglutination assay is accordingly provided where by controlling the orientation in which the rods aggregation either the $\Delta i_p$ or the FWHM can be used as the indicator for the detection an analyte.

The present specification further provides multi-component nanoparticles or rods composed for example of Au and having a segment that can be selectively activated with a capture probe of interest, and as such the segment can be configured to act as a locus for aggregation. The control over the signal created when the rods shaped particles aggregate advantageously makes agglutination assays much easier to multiplex. Using this dual signal, rather than creating a new aspect ratio rod for each analyte, similar sized rods can be used for two different targets simplifying particles synthesis. Further the provision of the nanoparticles 1 according to the present specification being configured to aggregate to form complexes of different shape and/or size makes multiplex detection much easier and far simpler. For example, a nanopore system or a tunable nanopore system may be used for multiplexed detection while optimised for one size of particles.

The ability to control the shape has not been shown using spherical beads and is a highly advantageous property of the rod shaped particles of the present specification. Further, a suitable detection system for example, a tunable nanopore system described above can advantageously distinguish also between rods and spheres. The length of the rod can be detected using FWHM. Aggregation of rods leads to an increase in size which is detected using the detector. Controlled aggregation of the rods can also lead to an increase in FWHM. The rods of the specification advantageously allow for a more sensitive assay and also for multiplexed detection.

The invention claimed is:

1. A method for detecting an analyte in a sample, the method comprising contacting the analyte in the sample with rod-shaped nanoparticles, each nanoparticle comprising a capture probe for capturing the analyte, and forming an aggregate of the analyte and two or more nanoparticles, detecting the analyte by detecting the shape and/or size of the aggregate, by detecting a full width half maximum (FWHM) signal, the signal being indicative of the time taken for each nanoparticle or aggregate to traverse a detector, each nanoparticle comprising multiple components, each nanoparticle comprising metal and having at least one segment of a selected material defining a location for the capture probe, such that the nanoparticles either aggregate end to end with the analyte to form an aggregate of detectably increased length, each nanoparticle having a diameter and a length, the diameter and the length controllable using a template deposition method of manufacture, each nanoparticle comprising a metal nanoparticle having a gold (Au) component and at least one segment of a selected metal material comprising one or more of nickel (Ni), cobalt (Co), iron (Fe), silver (Ag), palladium (Pd) and platinum (Pt), the segment having magnetic properties, the segment defining a location for the capture probe, wherein the segment is modified with a peptide that attaches only to the selected metal material of the segment and not to the Au component of the nanoparticle, and wherein the capture probe for the analyte is attached to the surface of the segment modified with the peptide;

wherein a location of the at least one segment is controlled during manufacture of each nanoparticle to direct the form of the aggregate to enable detection and identification of the analyte, wherein locating the segment at one end of each nanoparticle provides that two similar nanoparticles aggregate end to end with the analyte at the center of the aggregate to form an aggregate of detectably increased length, and wherein the presence of an analyte in the sample is detected by detecting the shape and/or size of the aggregate.

2. The method as claimed in claim 1 wherein each of the nanoparticles comprises a curved form.

3. The method as claimed in claim 2, wherein each of the nanoparticles comprises a cylindrical form.

4. The method as claimed in claim 1 wherein each of the nanoparticles comprises an aspect ratio greater than 1.

5. The method as claimed in claim 1 wherein the detecting the analyte comprises detecting the shape of the aggregate.

6. The method as claimed in claim 1 wherein the detecting the analyte comprises detecting the size of the aggregate.

7. The method as claimed in claim 1 wherein detecting the analyte comprises detecting the size of aggregates passing through a detector.

8. The method as claimed in claim 1 wherein detecting the analyte comprises detecting the shape of aggregates passing through a detector.

9. The method as claimed in claim 1 wherein the full width half maximum (FWHM) signal provides an indication of nanoparticle or aggregate length.

10. The method as claimed in claim 1 wherein each of the nanoparticles is a gold (Au) nanoparticle and the at least one segment is one or more of nickel (Ni), cobalt (Co), iron (Fe), silver (Ag), palladium (Pd), and platinum (Pt).

11. The method as claimed in claim 1, wherein each of the nanoparticles comprises a component having optical and magnetic properties.

12. A method for detecting an analyte in a sample, the method comprising:

providing a multicomponent nanoparticle comprising a gold (Au) surface, and at least one segment comprising one or more of nickel (Ni), cobalt (Co), iron (Fe), silver (Ag), palladium (Pd), and platinum (Pt) defining a location for a capture probe, wherein the segment is modified chemically to form the capture probe by attaching a peptide that attaches only to the material of the segment and not to the Au surface;

capturing an analyte with the capture probe and aggregating multiple nanoparticles with the analyte, the capture probe being a center for the aggregation of the nanoparticles with the analyte to form the aggregate having a detectable size and shape, and wherein the location of the segment is controlled as required during manufacture to allow for aggregates of different size and shape; such that the nanoparticle is configured to aggregate with the analyte and one or more nanoparticles; wherein the segment comprises a component having optical and/or magnetic properties;

wherein the nanoparticle has a rod shaped form or a generally cylindrical form, and an aspect ratio greater than 1;

each nanoparticle having dimensions determined by template deposition method parameters and wherein the parameters include reaction time and the template used for the deposition, wherein a location of the at least one segment is controlled during manufacture of each nanoparticle to direct the form of the aggregate to enable detection and identification of the analyte by detecting a full width half maximum (FWHM) signal, the signal being indicative of the time taken for each nanoparticle or aggregate to traverse a detector, and wherein locating the segment at one end of each nanoparticle provides that two similar nanoparticles aggregate end to end with the analyte at the center of the aggregate to form an aggregate of detectably increased length.

* * * * *